(12) United States Patent
Kyaw et al.

(10) Patent No.: US 12,607,590 B1
(45) Date of Patent: Apr. 21, 2026

(54) LIGHT-ASSISTED PORTABLE SENSOR FOR THE DETECTION OF HARMFUL PATHOGENS

(71) Applicant: SULTAN QABOOS UNIVERSITY, Al Khodh (OM)

(72) Inventors: Htet Htet Kyaw, Al Khodh (OM); Myo Tay Zar Myint, Al Khodh (OM); Mohammed Zahir Al-Abri, Al Khodh (OM); Salim Hamoud Al-Harthi, Al Khodh (OM)

(73) Assignee: SULTAN QABOOS UNIVERSITY, Al Khodh (OM)

( * ) Notice: Subject to any disclaimer, the term of this patent is extended or adjusted under 35 U.S.C. 154(b) by 0 days.

(21) Appl. No.: 19/312,856

(22) Filed: Aug. 28, 2025

(51) Int. Cl.
| | |
|---|---|
| *G01N 27/327* | (2006.01) |
| *G01N 27/30* | (2006.01) |
| *G01N 33/02* | (2006.01) |

(52) U.S. Cl.
CPC ....... *G01N 27/3278* (2013.01); *G01N 27/301* (2013.01); *G01N 33/02* (2013.01); *G01N 2333/245* (2013.01)

(58) Field of Classification Search
None
See application file for complete search history.

(56) References Cited

U.S. PATENT DOCUMENTS

2017/0038326 A1    2/2017 Motayed et al.

FOREIGN PATENT DOCUMENTS

| | | |
|---|---|---|
| CN | 107966560 A | 4/2018 |
| WO | 2020037269 A2 | 2/2020 |

OTHER PUBLICATIONS

K. Al-Yahmadi, et al., "Development of portable sensor for the detection of bacteria: effect of gold nanoparticle size, effective surface area, and interparticle spacing upon sensing interface", Discover Nano, 18(1): p. 45-61 + Suppl., March (Year: 2023).*

User's manual for Gamry Instruments Interface 1000, published Sep. 4 (Year: 2015).*

Homola, "Surface plasmon resonance sensors for detection of chemical and biological species." Chemical reviews 108.2 (2008): 462-493.

Pissuwan, et al. "Functionalised gold nanoparticles for controlling pathogenic bacteria." Trends in biotechnology 28.4 (2010): 207-213.

(Continued)

*Primary Examiner* — J. Christopher Ball
(74) *Attorney, Agent, or Firm* — Nath, Goldberg & Meyer; Joshua B. Goldberg

(57)    ABSTRACT

A light-assisted portable sensor for detecting harmful pathogens is provided. The portable sensor device includes a sensor chip; a conducting surface disposed on the sensor chip, tri-sodium citrate and chitosan-coated gold nanoparticles mounted on the conducting surface; a reference electrode disposed on the sensor chip; a counter electrode disposed on the sensor chip; and a signal amplifier electrically coupled with the sensor chip; wherein the tri-sodium citrate and chitosan-coated gold nanoparticles have a size between 10-25 nm, cover less than 35% of the conducting surface, and are spaced about 4 nm to about 15 nm apart to create an attractive environment for bacteria.

13 Claims, 10 Drawing Sheets

(56)  References Cited

OTHER PUBLICATIONS

Sugunan, et al. "Heavy-metal ion sensors using chitosan-capped gold nanoparticles." Science and Technology of Advanced Materials 6.3-4 (2005): 335.

Yang, et al. "Recent advances in colorimetric sensors based on gold nanoparticles for pathogen detection." Biosensors 13.1 (2022): 29.

* cited by examiner $$y = -7.62e^{-7}x + 1.0e^{-4}$$
$$R^2 = 0.9989$$

LIGHT-ASSISTED PORTABLE SENSOR FOR THE DETECTION OF HARMFUL PATHOGENS

BACKGROUND

1. Field

The disclosure of the present patent application relates to portable sensor devices and, particularly, to a portable sensor device and method for rapidly detecting harmful pathogens.

2. Description of the Related Art

Harmful pathogens such as bacteria, viruses, fungi, and parasites are biological agents that can cause illness. These pathogens can be found in various fruits, vegetables, processed foods, raw meat, surface water, and animals. The ingestion of pathogen-contaminated food and water causes sickness. The most common infectious pathogen is bacteria, and bacteria are the primary cause of hospitalizations and death. The conventional techniques for detecting bacteria in food products are cell culture and colony counting, simple and multiplex polymerase chain reaction, and immunological assays. The conventional detection methods are usually expensive, time consuming (sometimes it takes several days to receive results), laborious, complex processing steps and not suitable for field testing.

Thus, an inexpensive, portable, highly sensitivity, and user-friendly device for rapid detection of harmful pathogens solving the aforementioned problems is desired.

SUMMARY

The present disclosure relates to a light-assisted electrochemical sensing device and method of use wherein the device uses tri-sodium citrate and chitosan coated gold nanoparticles to enhance the detection of harmful pathogens. This device may be used in food industries, clinical diagnostic industries, pharmaceutical industries, and environmental protection industries where a rapid detection method is required or useful for harmful pathogens.

The present disclosure is also related to a method for the detection of harmful pathogens using tri-sodium citrate and chitosan coated gold nanoparticles loaded electrochemical sensors by shining light on the sensor to improve sensitivity of the sensor. The enhanced sensing activity may be achieved when the charge formation around tri-sodium citrate and chitosan coated gold nanoparticles may be maximized, in various embodiments, under light irradiation due to the size range of tri-sodium citrate and chitosan coated gold nanoparticles between 10-25 nm, the coverage of gold nanoparticles on the sample surface may be less than 35%, and the space between gold nanoparticles may be 4 nm to 15 nm.

According to an embodiment, a portable sensor device may include a sensor chip, a conducting surface disposed on the sensor chip, and tri-sodium citrate and chitosan coated gold nanoparticles mounted on the conducting surface. The portable sensor device may also include a reference electrode disposed on the surface of the sensor chip, a counter electrode disposed on the surface of the sensor chip; and a signal amplifier electrically coupled with the sensor chip. The tri-sodium citrate and chitosan coated gold nanoparticles on the conducting surface may have a size between 10-25 nm, cover less than 35% of the conducting surface;

and may be spaced between about 4 nm to about 15 nm apart to create attractive conditions for bacteria.

Another embodiment of the present disclosure includes a method of detecting bacteria in an environment using the portable sensor chip described herein. The method may include exposing the portable sensor chip to the environment, shining a visible light source on a surface of the portable sensor chip; activating the gold nanoparticles with the visible light source; and detecting bacteria using an electrochemical method. Exposing the portable sensor chip to the environment may include exposing the portable sensor chip to the environment under ambient conditions (room temperature and atmospheric pressure).

The present disclosure also includes a method of making a tailor-made sensor chip. The method may include cleaning the conducting surface; synthesizing tri-sodium citrate and chitosan coated gold nanoparticles; depositing the tri-sodium citrate and chitosan coated gold nanoparticles on the conducting surface; and adding the conducting surface to the sensor chip.

Other features of the present subject matter will become readily apparent upon further review of the following specification.

3

Figure 11A:
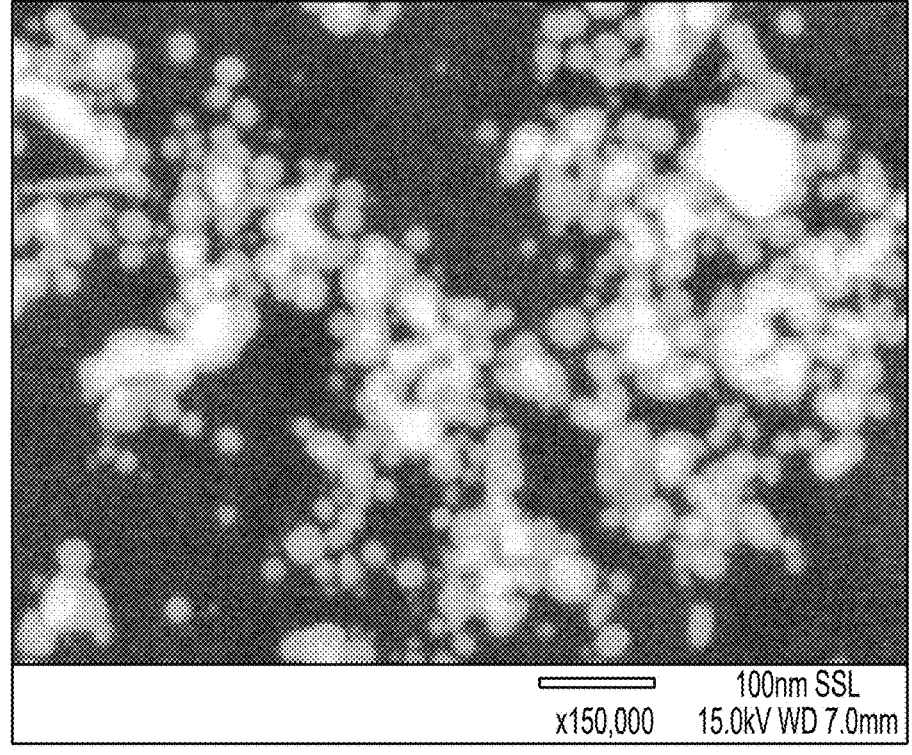
FIG. 11A is an electron microscope photograph of gold nanoparticles capped only with Chitosan.
Figure 11B:
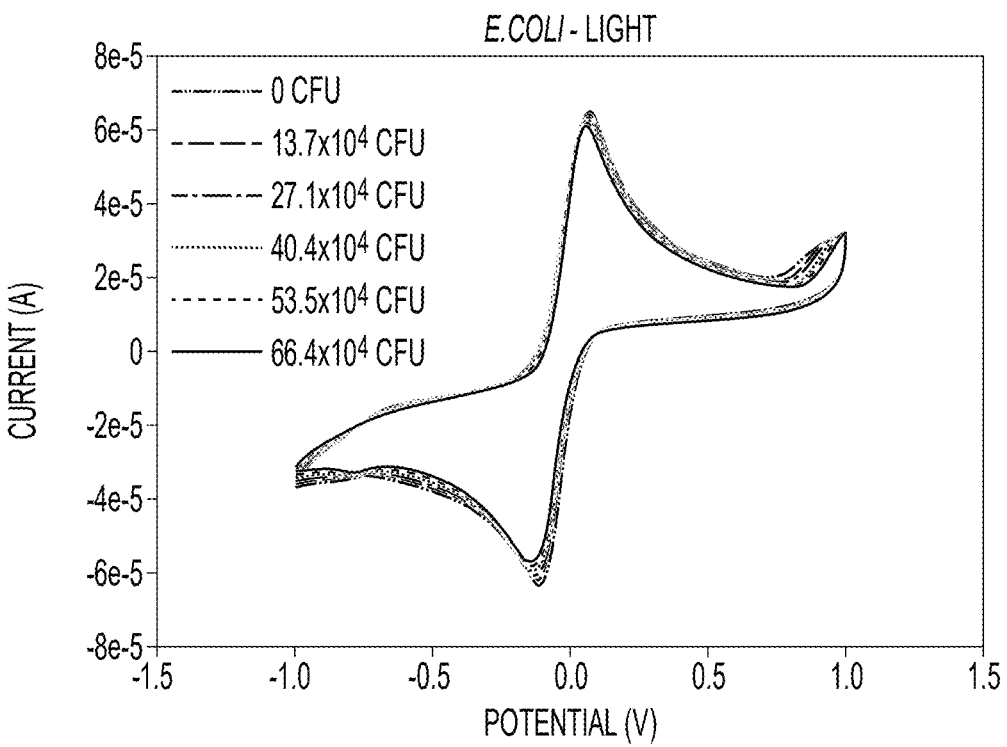

FIG. 11B is a chart showing the gram-negative bacteria *Escherichia coli* (*E. coli*) detection using cyclic voltammetry technique using the nanoparticles of FIG. 11A.

Figure 11C:
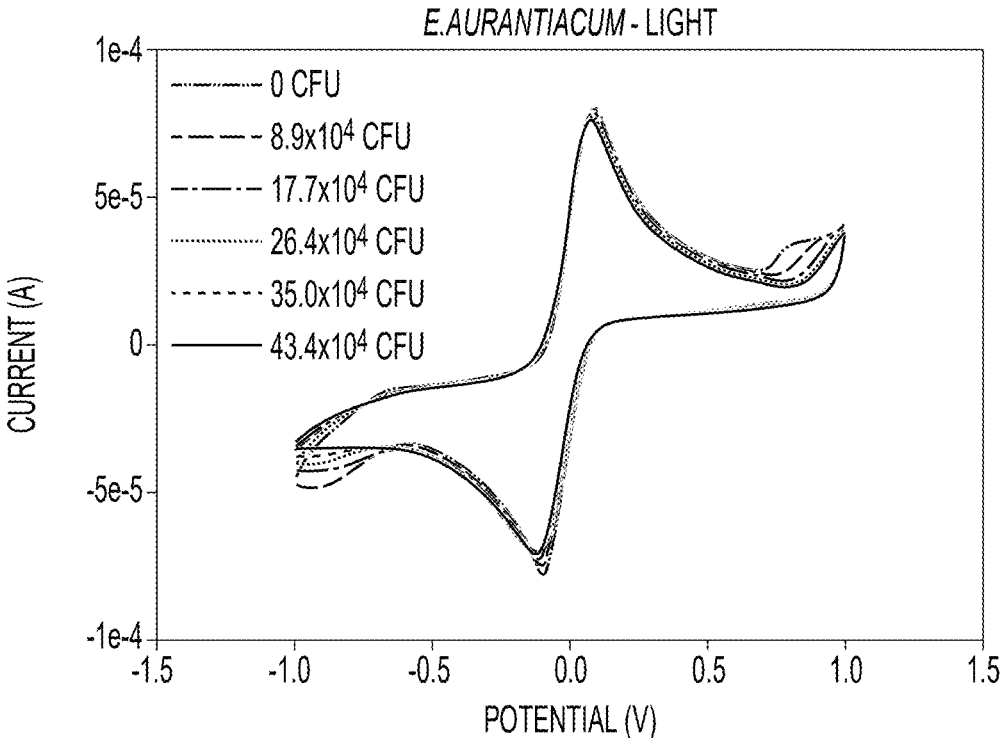

FIG. 11C is a chart showing the gram-positive bacteria *Exiguo-bacterium aurantiacum* (*E. aurantiacum*) detection using cyclic voltammetry technique using the nanoparticles of FIG. 11A.

Similar reference characters denote corresponding features consistently throughout the attached drawings.

DETAILED DESCRIPTION OF THE PREFERRED EMBODIMENTS

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions, products, or systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present disclosure relates to a portable, light-assisted electrochemical sensing device and method of using the device for detection of harmful pathogens. The device includes a sensor chip, and tri-sodium citrate and chitosan coated gold nanoparticles loaded on a conductive surface of the sensor chip. The device and method of preparing the device may offer a simple, cost effective, easy and enhanced method for detection of pathogens using light and electrochemical sensing. The device and method may be used in food industries, clinical diagnostic industries, pharmaceutical industries, and environmental protection industries where a rapid detection method would be desired for harmful pathogens. The present device allows for rapid and point of care detection of harmful pathogens, such as harmful bacteria, in different fields of application.

Figure 1:
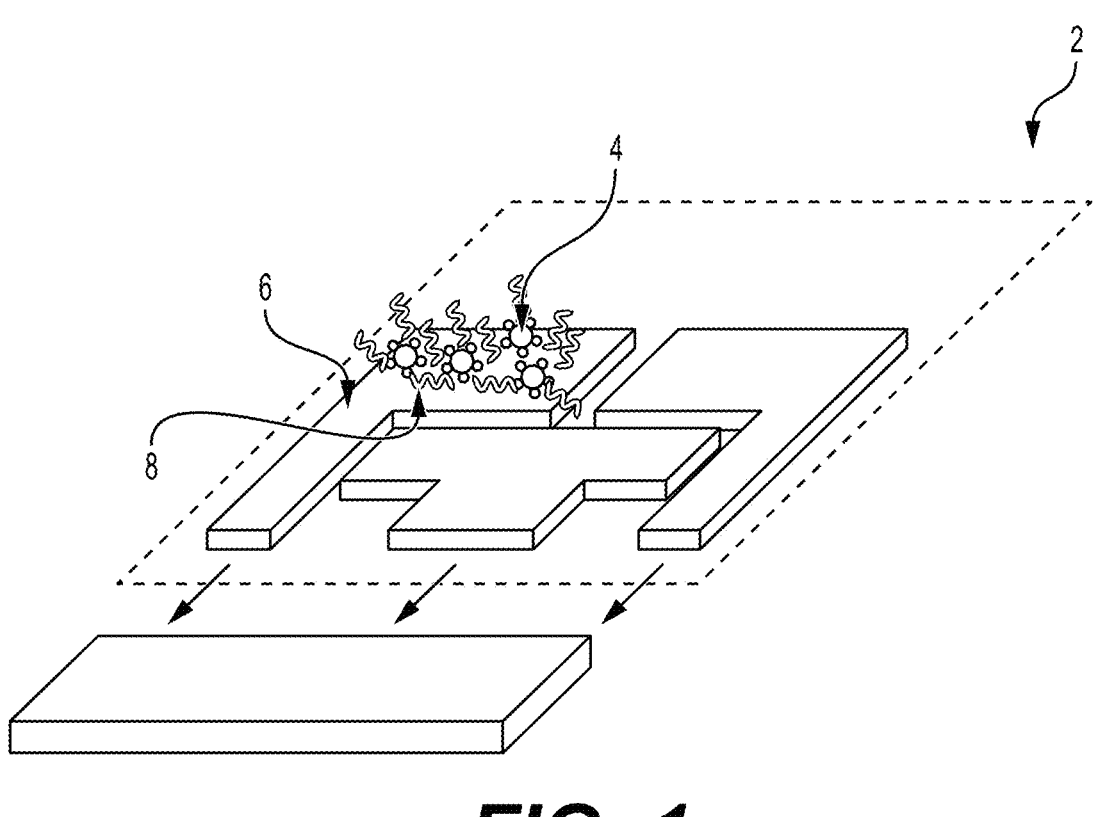
FIG. 1 is a top perspective view of an embodiment of a portable sensor as described herein.

An embodiment of a portable sensing device 2, as described herein, is illustrated in FIG. 1. As shown in FIG. 1, the device 2 includes tri-sodium citrate and chitosan-coated gold nanoparticles 4 mounted on a conducting surface 6 disposed on a sensor chip. A space between adjacent ones of the tri-sodium citrate and chitosan-coated gold nanoparticles 4 can be a distance 8 that is in a nanometer range (e.g., inter-particle spacing or the distance between the surface of two particles). For example, a distance between adjacent gold nanoparticles can range from about 4 nm to about 15 nm. In an embodiment, the gold nanoparticles cover about 35% or less of the conductive surface. For example, the gold nanoparticles can cover about 15% to about 35% of the conductive surface. A size of the tri-sodium citrate and chitosan-coated gold nanoparticles can range from about 10 nm to about 25 nm. This range is determined by the initial concentration of Au ions and the stabilizing and reducing agent (tri-sodium citrate and chitosan) concentrations. In addition, a volume of tri-sodium citrate and chitosan coated-gold nanoparticles per unit area of the conducting surface is an important factor in achieving the desired surface coverage, e.g., about 35% or less, of gold nanoparticles on the sample surface. The tri-sodium citrate and chitosan-coated gold nanoparticles may be uniformly spaced to increase affinity of a harmful pathogen, e.g., a bacteria, to the conductive surface.

Figure 2:
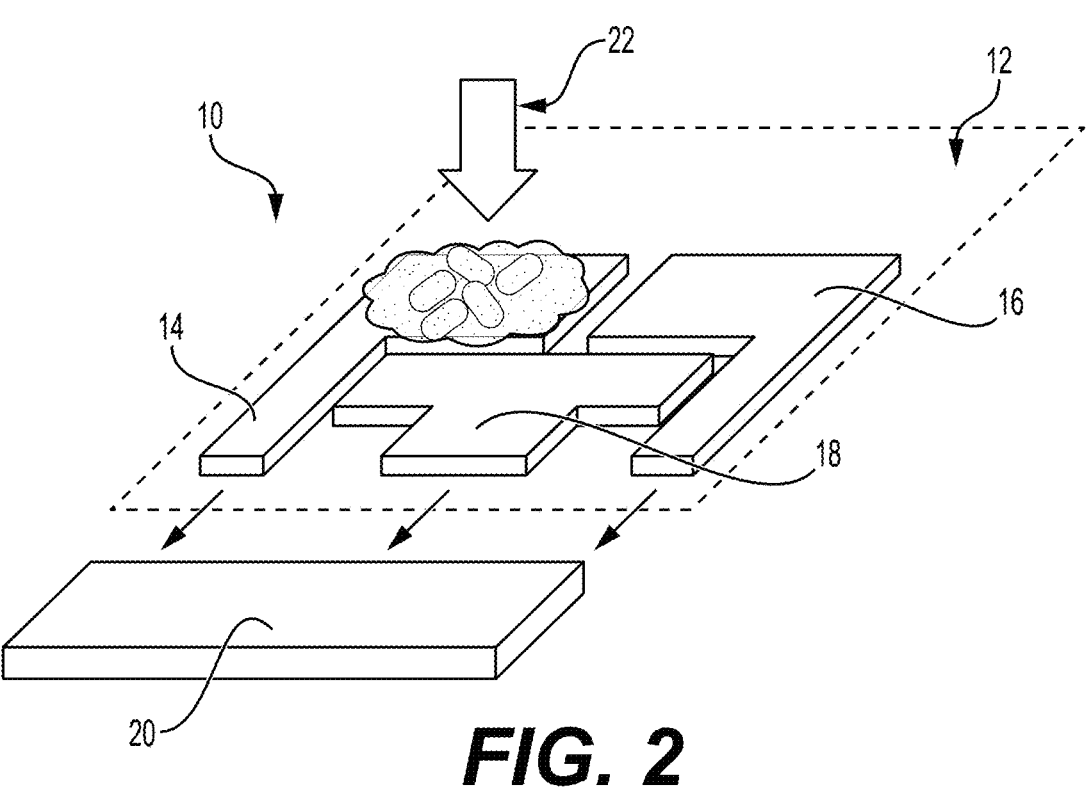
FIG. 2 is a top perspective view of an embodiment portable sensor with visible light.

FIG. 2 depicts an embodiment of the portable sensor device 10 for detecting harmful bacteria, showing a sensor chip 12 and a conducting surface 14 disposed on the sensor chip 12. Tri-sodium citrate and chitosan-coated gold nanoparticles are mounted on the conducting surface 14. The tri-sodium citrate and chitosan-coated gold nanoparticles may have a size ranging from about 10 nm to about 25 nm. The tri-sodium citrate and chitosan-coated gold nanoparticles may cover about 35% or less of the conducting surface, e.g., about 15% to about 35% of the conducting surface, and may be spaced at least about 4 nm to about 15 nm apart. A uniform interparticle spacing of about 4 nm to about 15 nm may optimize conditions for drawing bacteria to the conductive surface. For example, it is believed that shining light on the conductive surface causes localized heating around the gold nanoparticles, creating a more attractive environment for bacteria and allowing for detection of more bacteria. The portable sensor device 10 can include a reference electrode 16 and a counter electrode 18 disposed on a surface the sensor chip 12. The portable sensor device 10 may include a signal amplifier 20 electrically coupled to the sensor chip 12.

As illustrated, in various embodiments the portable sensor device may also include a visible light source 22. In some embodiments, the visible light source may be coupled with the portable sensor device. In other embodiments, a visible light source may be provided by a separate device.

The portable sensor device may be used in a method of detecting bacteria in an environment. The method may include exposing the portable sensor chip to the environment, shining a visible light source on a surface of the portable sensor chip; activating the gold nanoparticles with the visible light source; and detecting bacteria using an electrochemical method. Exposing the portable sensor chip to the environment may include exposing the portable sensor chip to the environment under ambient conditions (room temperature and atmospheric pressure).

In various embodiments, the harmful pathogens may be bacteria.

In various embodiments, the visible light source may be separate from the sensor chip of the portable sensor device.

In some embodiments, the visible light source may be physically and electronically coupled with the sensor chip.

In some embodiments, the electrochemical method may include detecting a current change using, e.g., using cyclic voltammetry, generated when the harmful pathogens are drawn to the tri-sodium citrate and chitosan-coated gold nanoparticles on the conductive surface of the sensor chip. Bacteria in particular have an affinity for the tri-sodium citrate and chitosan coated gold nanoparticles and the affinity is enhanced when the conductive surface is irradiated with visible light.

The method may include creating an inter-particle spacing in which the charge formation around the gold nanoparticles is maximized when the tri-sodium citrate and chitosan coated gold nanoparticles interact with visible light from the visible light source.

In various embodiments, the charge formation may be maximized when the tri-sodium citrate and chitosan coated gold nanoparticles have an interparticle spacing of about 4 nm to about 15 nm.

In some embodiments, the charge formation may be maximized when the tri-sodium citrate and chitosan-coated gold nanoparticles have a size ranging from about 10 nm to about 25 nm.

In other embodiments, activating the tri-sodium citrate and chitosan-coated gold nanoparticles includes maximizing a charge formation around the tri-sodium citrate and chitosan coated gold nanoparticles to increase the attraction of bacteria to the conducting surface.

In some embodiments, the environment may be a food product. In other embodiments, the food product may be selected from the group consisting of fruits, vegetables, processed foods, raw meat, surface water, and animals. Other environments may be analyzed using the portable sensor described herein, such as by non-limiting example, countertops, sinks, and other surface where food may be prepared or eaten. The portable sensing device may also be used in healthcare situations.

In various embodiments, the harmful pathogen that can be detected may be a bacteria and the bacteria may include *E. coli* and *E. aurantiacum*. In other embodiments, any bacteria, whether gram-positive or negative, may be detected due to the sensing nature of the conducting surface, which is sensitive enough to detect changes in its surrounding environment.

Figure 3:
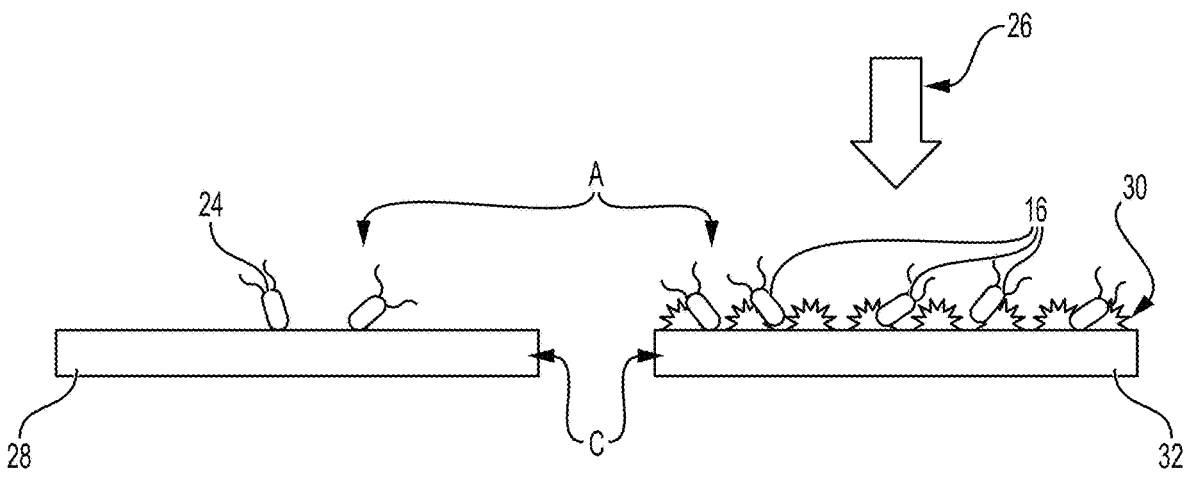
FIG. 3 is a schematic diagram of the effect of visible light on attracting pathogens.

FIG. 3 includes a diagram illustrating the increase of bacteria 24 on the conducting surface 28 after the conducting surface 28, loaded with loaded with tri-sodium citrate and chitosan coated gold nanoparticles, is illuminated with visible light 26.

As shown, only a few bacteria 34 are attracted to the conducting surface 36 without light irradiation, while significantly more bacteria 42 are attracted to the tri-sodium citrate and chitosan coated gold nanoparticles 38 on the conducting surface 36 with visible light 44 irradiation. When bacteria contact the tri-sodium citrate and chitosan-coated gold nanoparticles on the conducting surface, an attractive force between the tri-sodium citrate and chitosan-coated gold nanoparticles and bacteria may take place. Shining visible light on the sensing/conducting surface increases sensitivity of detection of bacteria due to interactions between the tri-sodium citrate, the chitosan-coated gold nanoparticles and the light. Moreover, light shining on the gold nanoparticles may cause localized heating/warming around the nanoparticles, creating attractive conditions for the bacteria.

The sensor chip includes a sensing electrode and a counter electrode separated by a thin electrolytic layer. Generally, bacteria drawn to the gold nanoparticles undergo a redox reaction on a suitable electrode, generating an electrical current depending on the gas concentration. The sensitive layer from the sensing surface plays the role of a receptor. Tri-sodium citrate and chitosan-coated gold nanoparticles act as a sensing material and visible light is used to enhance the sensitivity of the tri-sodium citrate and chitosan-coated gold nanoparticles for the detection of bacteria. The method described herein is based on pure light activation of properly dispersed tri-sodium citrate and chitosan coated gold nanoparticles without any bio-recognition. Here, properly spaced means tri-sodium citrate and chitosan coated gold nanoparticles having sizes ranging from about 10 nm to about 25 nm and an inter-particle spacing of about 4 nm to about 15 nm.

The present device includes fixed or immobile tri-sodium citrate and chitosan-coated gold nanoparticles on the conductor/sensor surface. The present detection method includes an electrochemical method activated with visible light and without agglomerating gold nanoparticles.

Figure 4A:
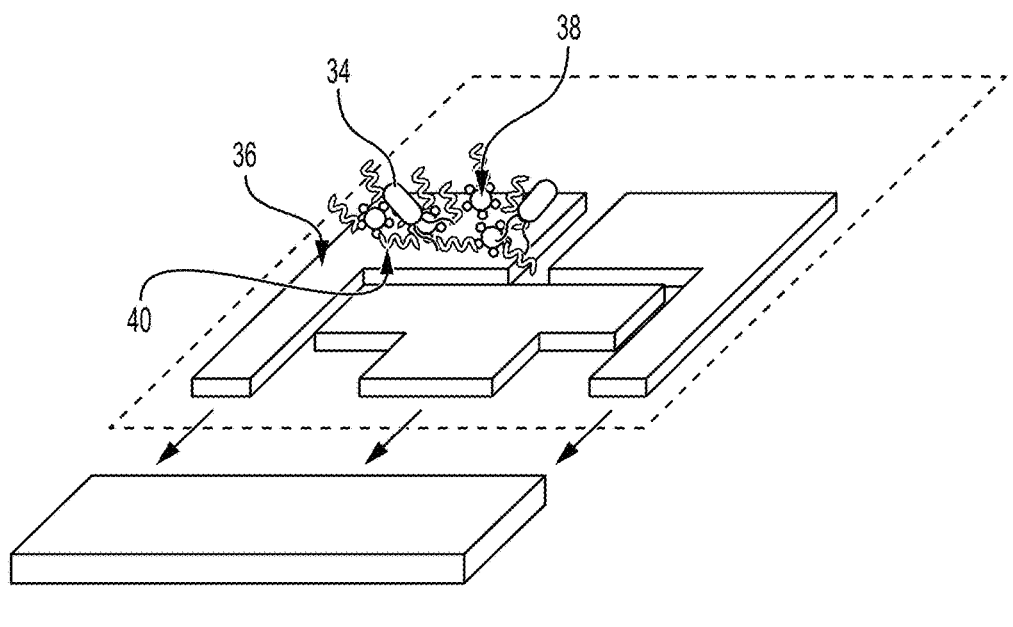
FIGS. 4A and 4B are a comparison of the effect of visible light on attracting pathogens using the top perspective views of embodiment portable sensors showing a detailed structure of tri-sodium citrate and chitosan coated gold nanoparticles mounted on the sensing surface.
Figures 4B, 5:
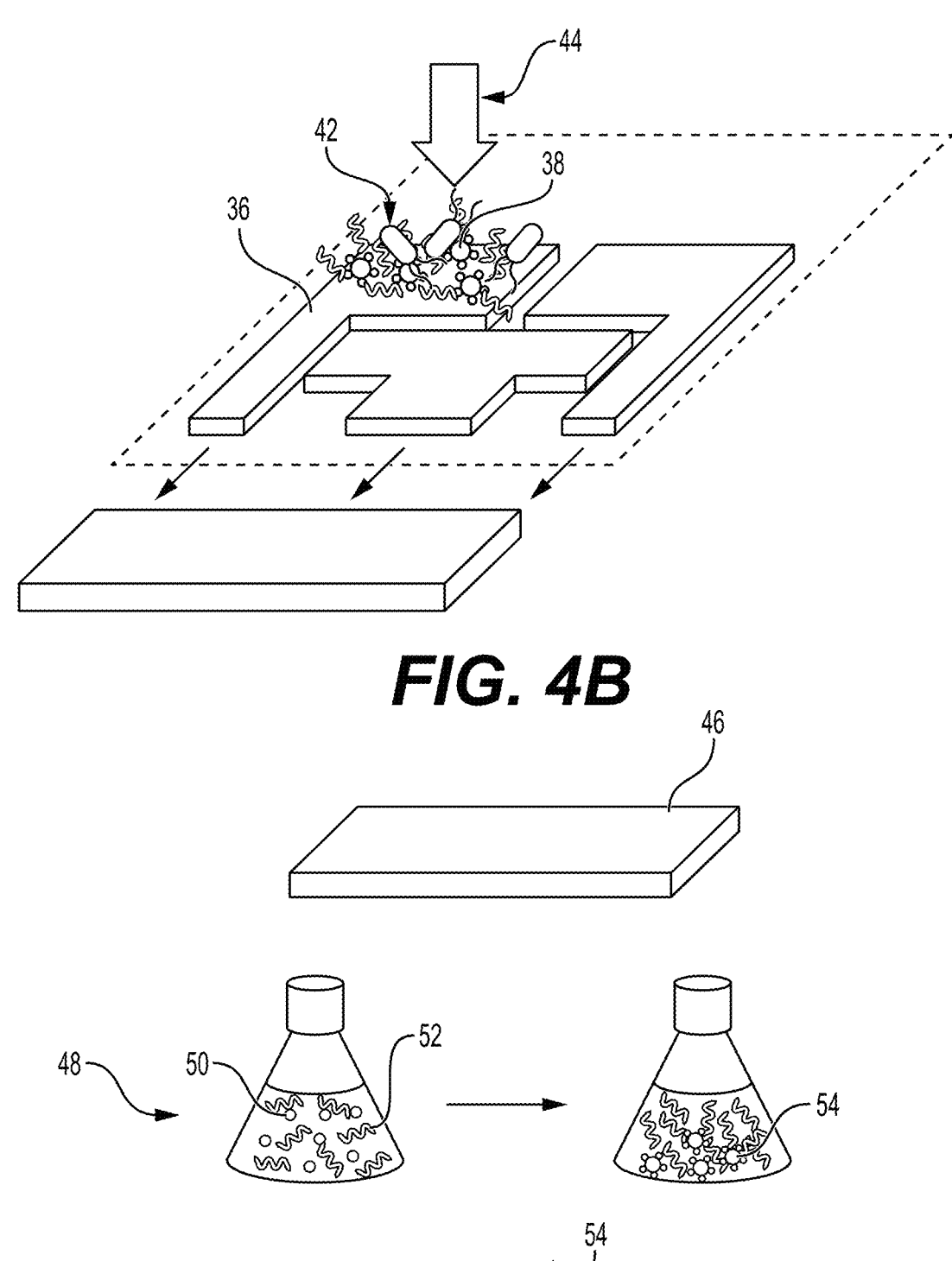
FIG. 5 is a schematic showing an embodiment of a method of making an embodiment of a portable sensor device including tri-sodium citrate and chitosan coated gold nanoparticles.

A method of making the sensor chip described herein is illustrated in FIG. 5. The method may include cleaning the conducting surface 46. In various embodiments, the conducting surface may be cleaned using any of the following: soap, water, deionized water, ethanol, and acetone. The method also includes synthesizing 48 tri-sodium citrate 50 and chitosan 52 coated-gold nanoparticles 54 and depositing 56 the tri-sodium citrate and chitosan coated gold nanoparticles 54 on the conducting surface 46 and mounting the conducting surface to the sensor chip.

In various embodiments, synthesizing the tri-sodium citrate and chitosan coated-gold nanoparticles includes using a wet chemical method.

In some embodiments, synthesizing the tri-sodium citrate and chitosan-coated gold nanoparticles includes adding a chitosan solution to gold (III) chloride trihydrate to create a first mixture. Adding deionized water is to the first mixture to create a second mixture. Heating the second mixture is heated to a boil and boiling is maintained for a period of time. When the color of the gold-chitosan mixture changes to a pale yellow, tri-sodium citrate is added to the boiling second mixture and maintained until the second mixture turns red. Here, tri-sodium citrate and chitosan may act as a stabilizing and a reducing agent. The mixture's color may change to ruby red after at least about seven minutes of boiling, forming a collodial solution. The colloidal solution can then be quenched in an ice bath to stop the reaction.

In other embodiments, depositing the tri-sodium citrate and chitosan-coated gold nanoparticles on the conducting surface includes drop-casting three successive layers of a solution containing 26.4 μL of tri-sodium citrate and chitosan coated gold nanoparticles on the conducting surface and drying the conducting surface. The conducting surface may be dried at a temperature of at least about 80° C. for at least about 14 hours. The conducting surface may have an area of at least about 1 cm².

The method may further include drying the sensor chip at room temperature for at least about 30 minutes.

In various embodiments, the tri-sodium citrate and chitosan-coated gold nanoparticles have a size ranging from about 10 nm to about 25 nm.

In some embodiments, the tri-sodium citrate and chitosan-coated gold nanoparticles cover less than 35% of the conducting surface.

In other embodiments, the tri-sodium citrate and chitosan-coated gold nanoparticles are spaced about 4 nm to about 15 nm apart to create an attractive environment for bacteria. The present teachings are illustrated by the following examples.

Example 1

Making a Portable Sensor Device

The conducting surface was cleaned using soap water, deionized (DI) water, ethanol and acetone. Synthesis of the gold nanoparticles was done using a wet chemical method. Specifically, 1% (w/v) chitosan solution was added to 1 mL of 20 mM of gold (III) chloride trihydrate. Under continuous stirring, 47.5 mL of DI water was added to the gold-chitosan mixture, which was then heated to a boil. When the color of the gold-chitosan mixture changed to pale yellow, 2.5 mL of 56 mM tri-sodium citrate was added, and the solution continued to boil. Here, tri-sodium citrate and chitosan acted as a stabilizing and reducing agent. The solution's color changed to ruby red after seven minutes, the colloidal solution was quenched in an ice bath to stop the reaction. The gold nanoparticles were mounted on the conducting/sensing surface by dropping the prepared gold nanoparticle solution at room temperature. Three successive layers of a solution containing 26.4 μL of gold nanoparticles were dropped/cast onto the working electrode surface. The working electrode surface area had a surface area of 1 cm² in order to achieve less than 35% coverage of the sample surface, and the distance between the gold nanoparticles was between 4 and 15 nm.

After dropping the nanoparticles on the conducting surface, the sensor chip was dried at room temperature for 30 minutes. Then, for better attachment of the gold nanoparticles on the conducting surface, the sensor chip was kept in the oven at 80° C. for approximately 14 hours.

A proper inter-particle spacing was achieved when the charge formation around the gold nanoparticles upon visible light irradiation was maximized. The maximum charge formation around gold nanoparticles caused the sensing surface to be highly sensitive by attracting more bacteria to the gold nanoparticles.

Example 2

Detecting Bacteria

Figure 6:
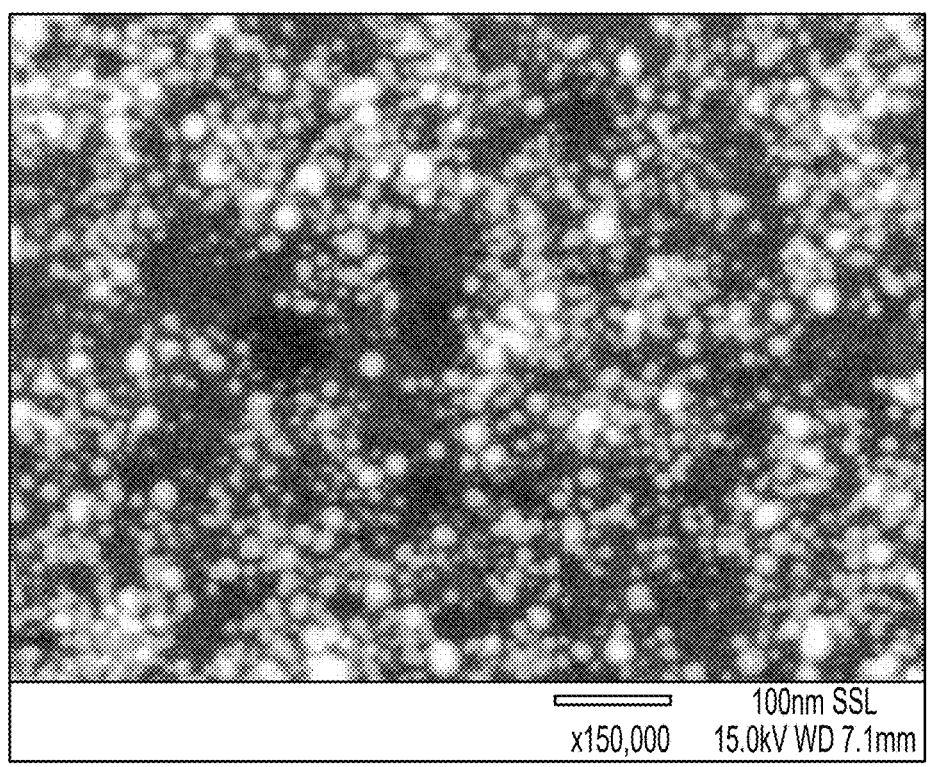
FIG. 6 is an electron micrograph of chitosan and tri-sodium citrate capped gold nanoparticles as described herein.

A presence of bacteria in a sample was determined by contacting the sample with the conductive surface of the sensor chip and irradiating the conducting surface of the sensor chip with visible light. It was determined that bacteria were present in the sample when a current change was detected using cyclic voltammetry An electron microscope scan of chitosan and tri-sodium citrate capped gold nanoparticles is illustrated in FIG. 6. The nanoparticles shown in FIG. 6 demonstrated an improved current response when compared with gold nanoparticles capped only with chitosan (shown in FIG. 11A). The nanoparticles shown in FIG. 11A are gold nanoparticles on a conducting surface having a size range of 10-50 nm with non-uniform coverage and non-uniform spacing. The nanoparticles shown in FIG. 11A had a lower current response (see FIG. 11B) as compared to the nanoparticles shown in FIG. 6 (see FIGS. 7C and 9C).

Figure 7A:
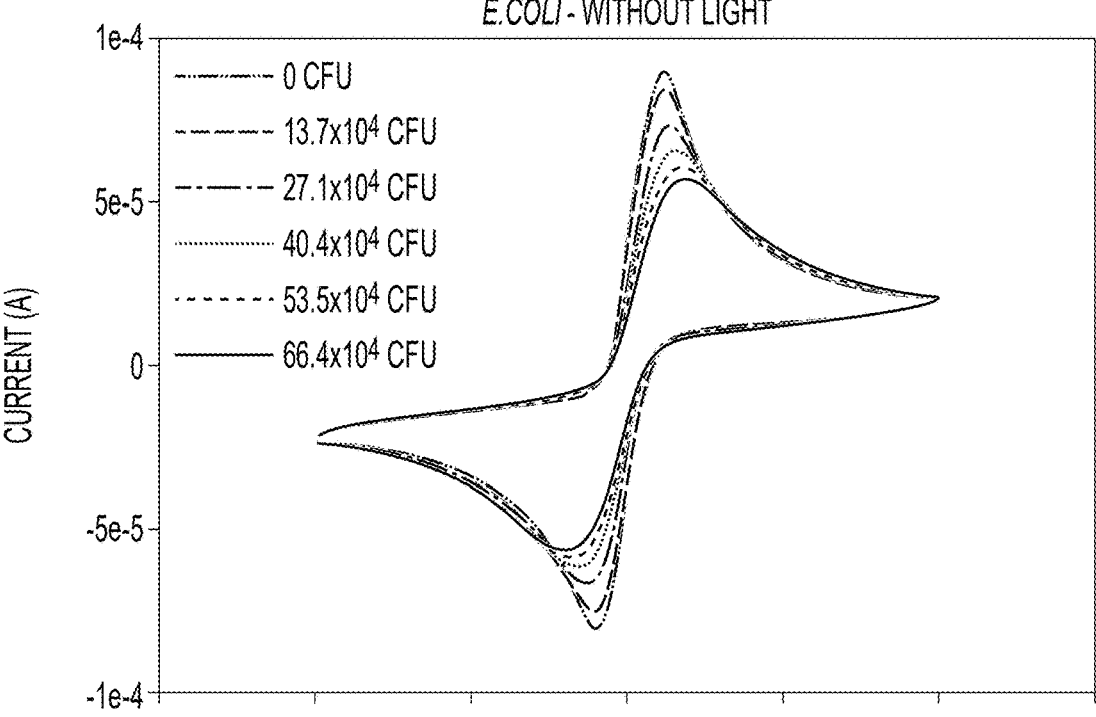
FIG. 7A is a chart showing the gram-negative bacteria *Escherichia coli* (*E. coli*) detection using cyclic voltammetry technique without light.
Figure 7B:
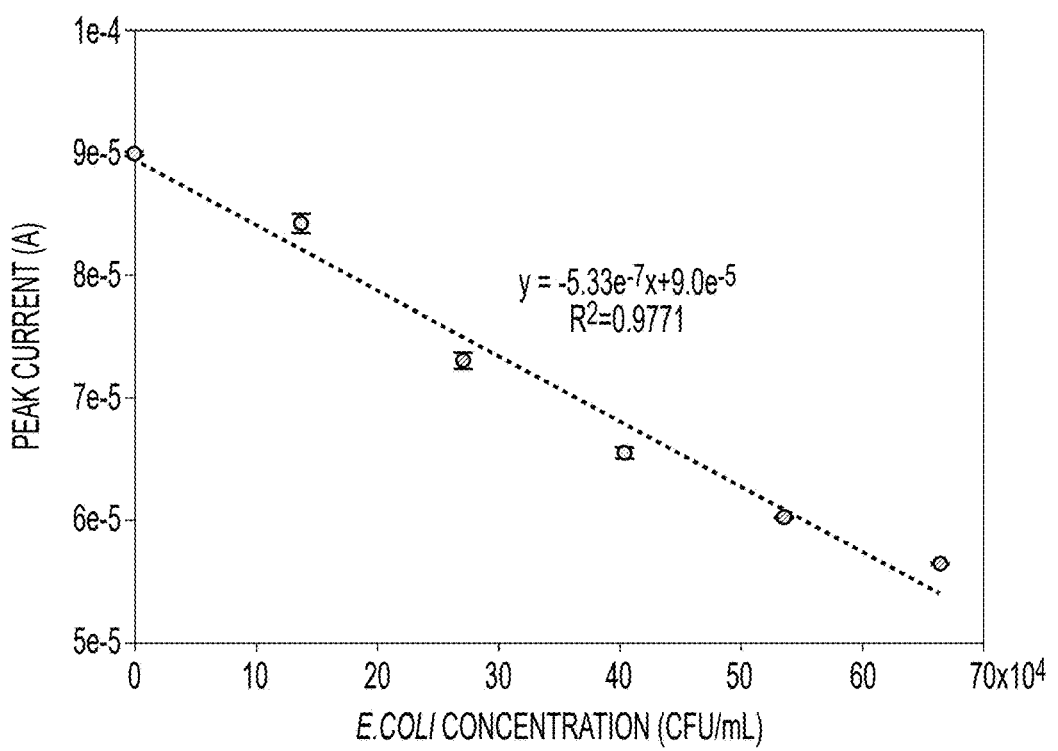
FIG. 7B is a plots of the peaks in FIG. 7A.
Figure 7C:
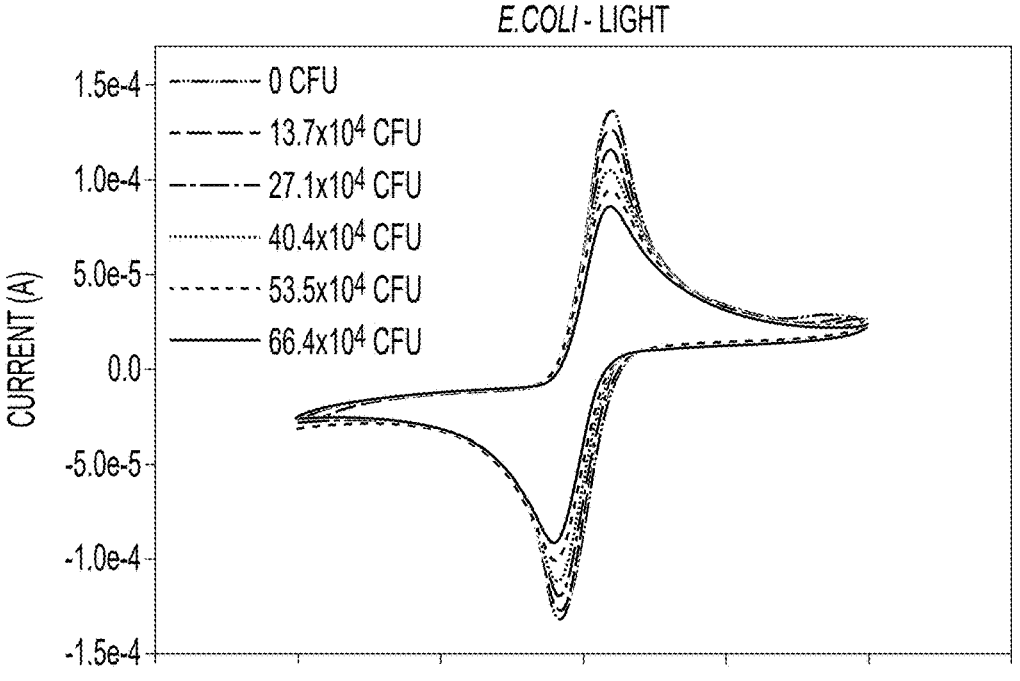
FIG. 7C is a chart showing the gram-negative bacteria *Escherichia coli* (*E. coli*) detection using cyclic voltammetry technique with light.
Figure 7D:
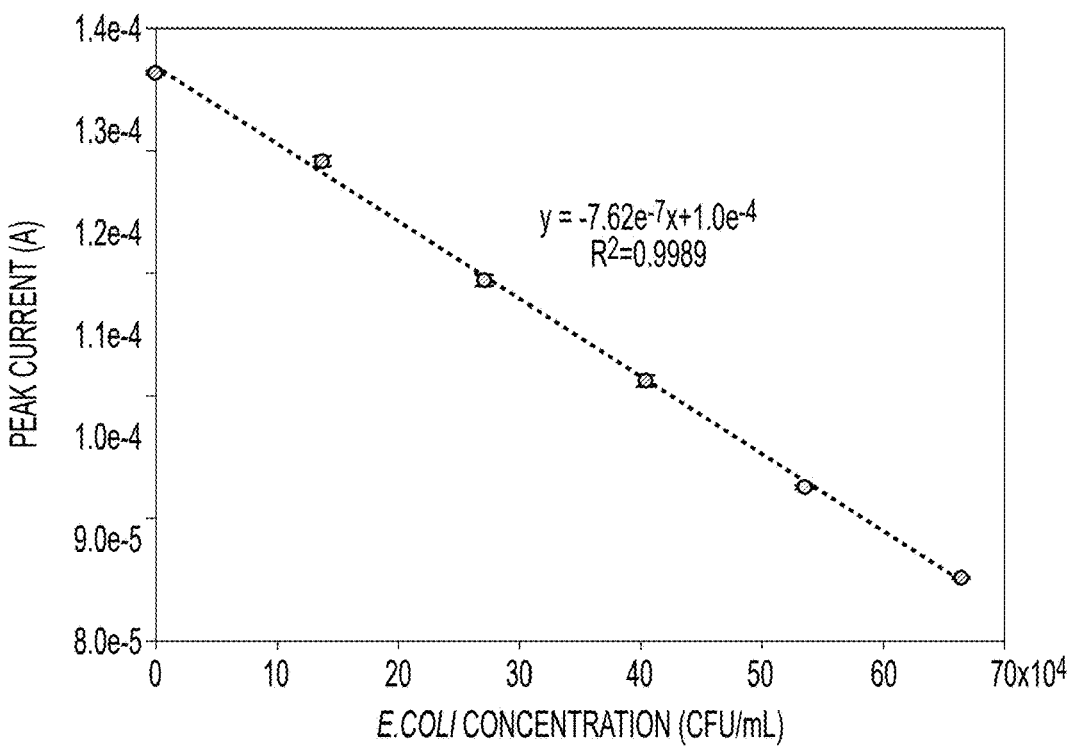
FIG. 7D is a plots of the peaks in FIG. 7C.
Figure 8:
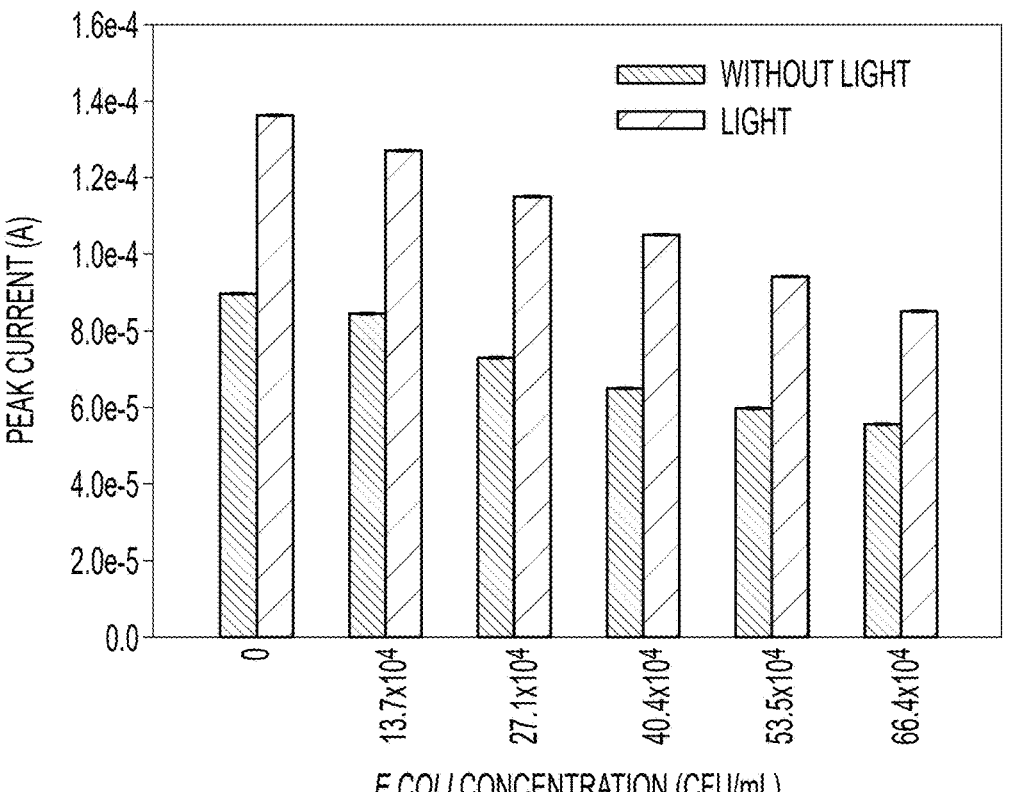
FIG. 8 is a histogram chart showing the reduction in peak current versus *E. coli* concentrations from FIGS. 6A-6D.

Further tests were run comparing the detection of bacteria by the nanoparticles shown in FIG. 6 with and without irradiation with visible light. FIGS. 7A-7D shows graphs illustrating the detection of gram-negative bacteria *Escherichia coli* (*E. coli*). The reduction in peak current response to *E. coli* without irradiation with visible light (FIG. 7A) when compared to the response to *E. coli* with irradiation with visible light (FIG. 7C) was understood to result primarily from the attraction of the *E. coli* bacteria towards the chitosan and tri-sodium citrate capped gold nanoparticles mounted on the sensing surface resulting from irradiation with visible light. The plot of peak current associated with different *E. coli* concentrations showed a linear trend with a faster slope in the *E. coli* irradiated with visible light (FIG. 7D) as compared to the slope corresponding to the sample tested without irradiation with visible light (FIG. 7B). The histogram shown in FIG. 8 shows the reduction in peak current as a function of *E. coli* concentration.

Figure 9A:
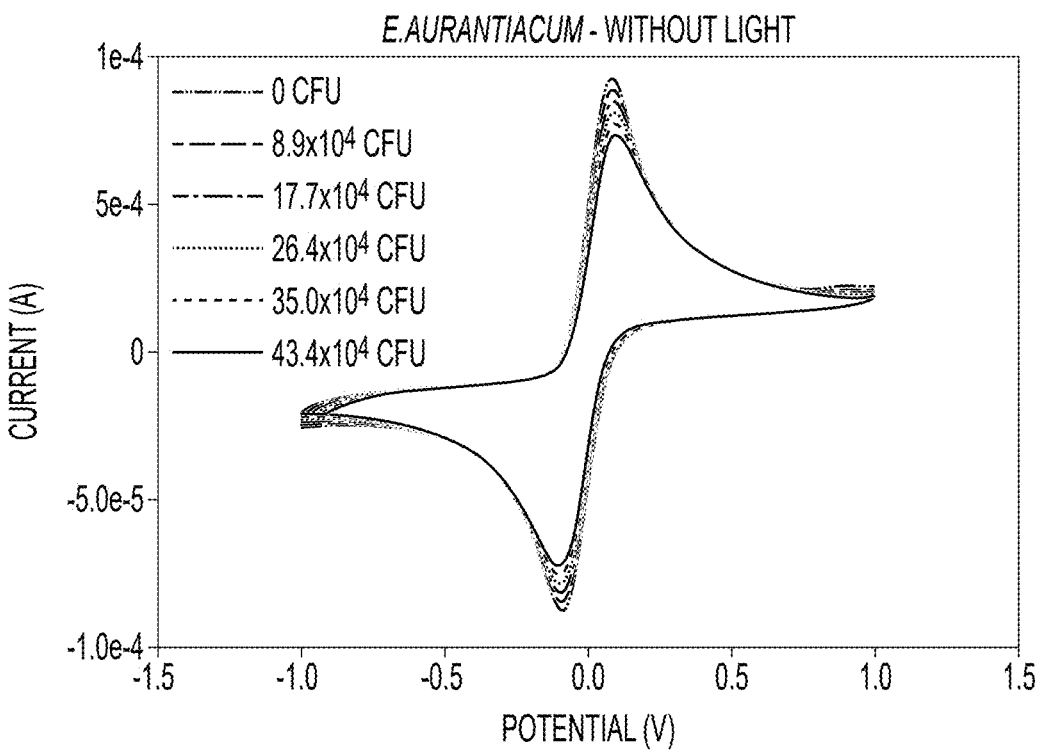
FIG. 9A is a chart showing the gram-positive bacteria *Exiguo-bacterium aurantiacum* (*E. aurantiacum*) detection using cyclic voltammetry technique without light.
Figure 9B:
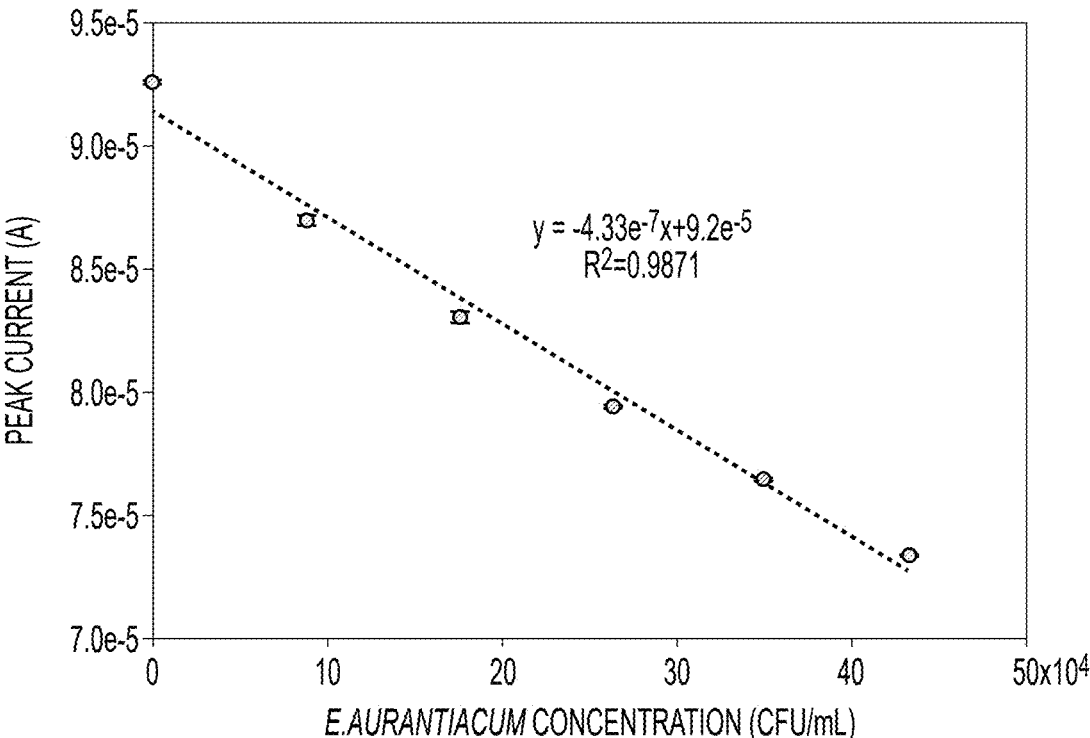
FIG. 9B is a plots of the peaks in FIG. 9A.
Figure 9C:
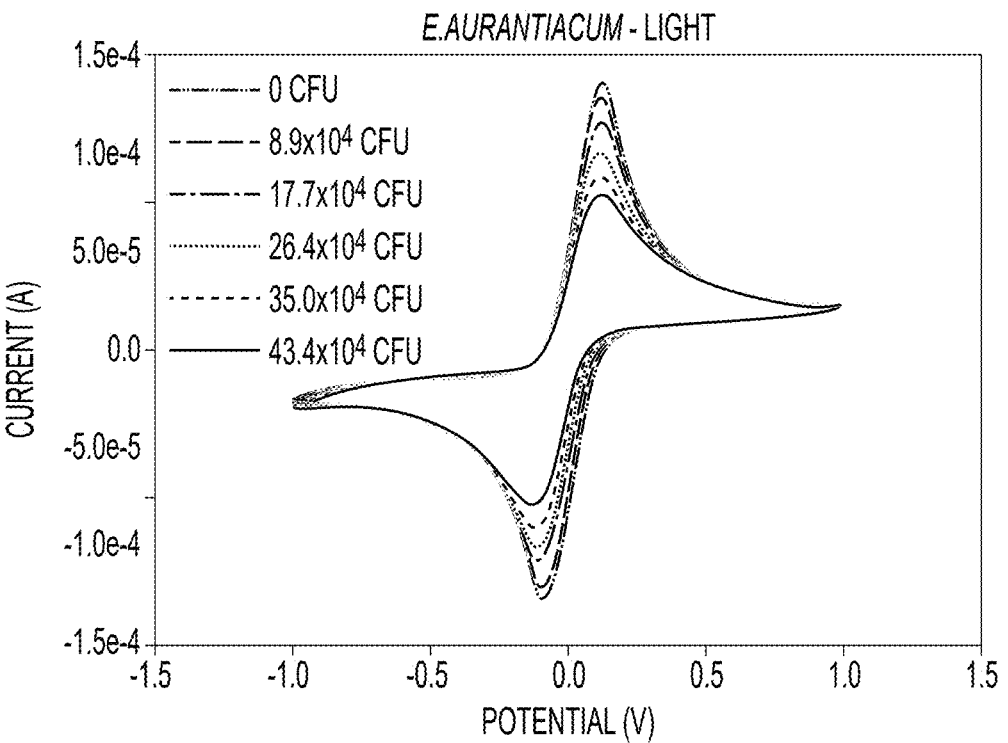
FIG. 9C is a chart showing the gram-positive bacteria *Exiguo-bacterium aurantiacum* (*E. aurantiacum*) detection using cyclic voltammetry technique with light.
Figure 9D:
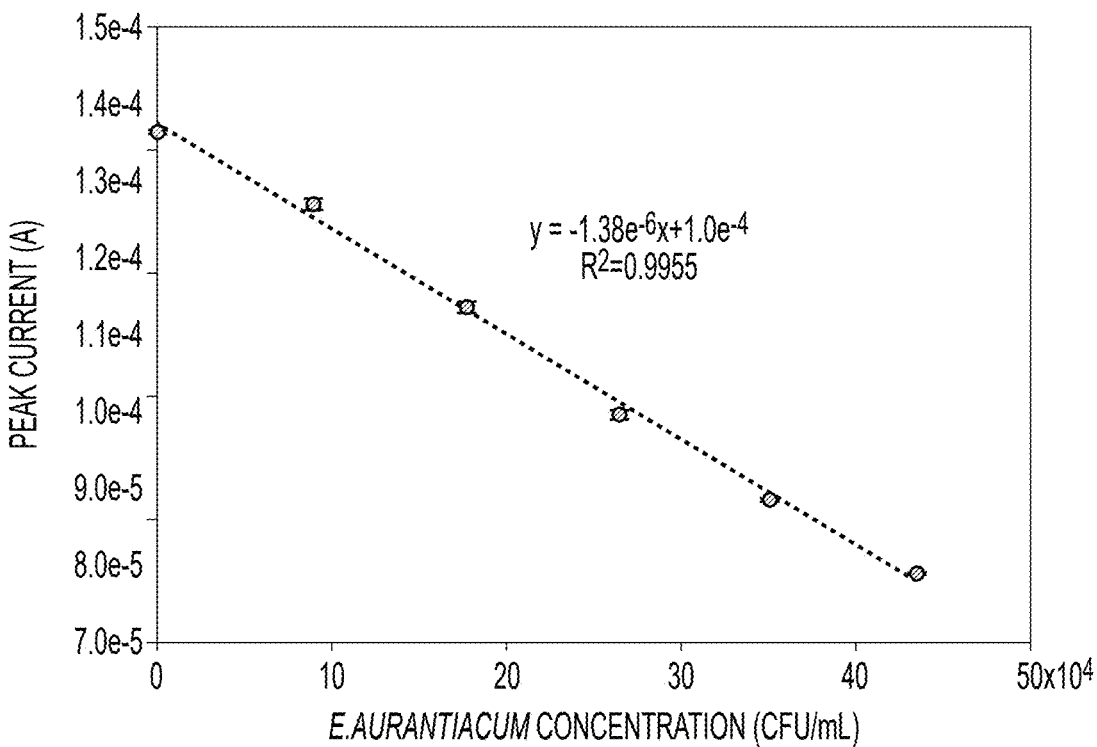
FIG. 9D is a plots of the peaks in FIG. 8C.
Figure 10:
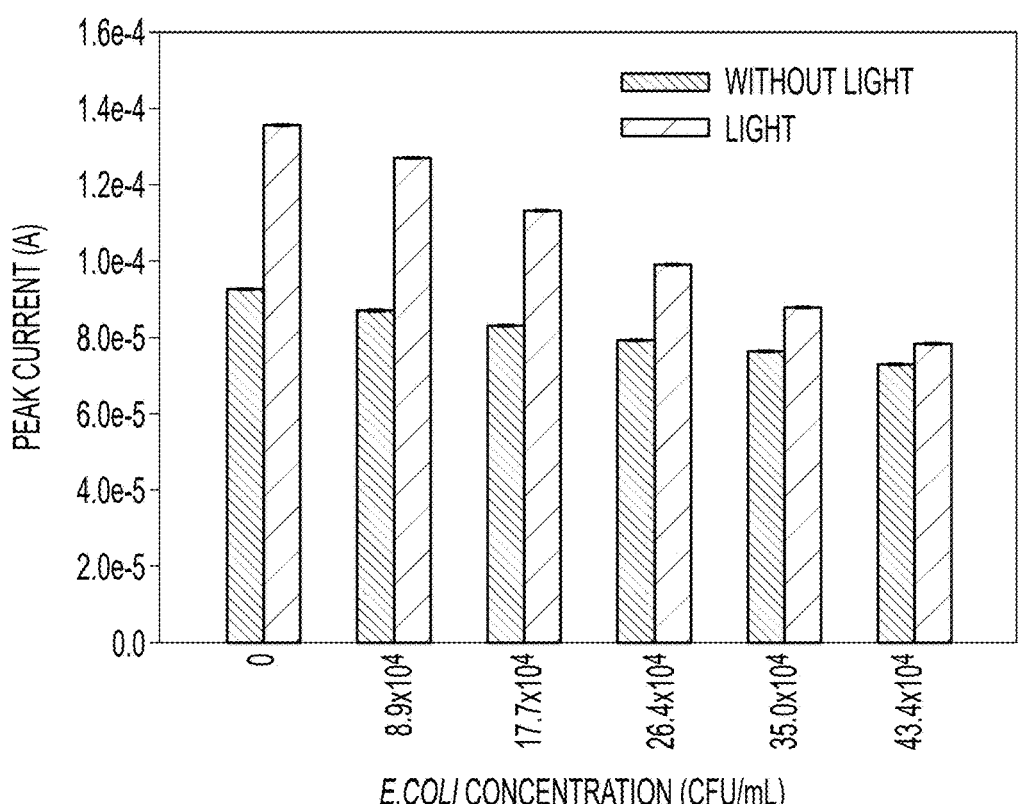
FIG. 10 is a histogram chart showing the reduction in peak current versus *E. aurantiacum* concentrations from FIGS. 8A-8D.

Similar tests were conducted for the detection of *E. aurantiacum*. FIGS. 9A-9D show detection of the gram-positive bacteria *Exiguo-bacterium aurantiacum* (*E. auran-tiacum*) using the cyclic voltammetry technique. The reduction in peak current response in *E. aurantiacum* tested without irradiation with visible light (FIG. 9A), when compared with the peak current response for *E. aurantiacum* tested with irradiation with visible light (FIG. 9C) was understood to result primarily from the attraction of bacteria towards the chitosan and tri-sodium citrate capped gold nanoparticles mounted on the sensing surface resulting from irradiation with visible light. The plot of peak current associated with different *E. aurantiacum* concentrations showed a linear trend with a faster slope in the *E. auran-tiacum* irradiated with visible light (FIG. 9D) as compared to the slope corresponding to the sample tested without irradiation with visible light (FIG. 9B). The histogram shown in FIG. 10 shows the reduction in peak current as a function of *E. aurantiacum* concentration. These results demonstrate that the sensing technique was more selective toward *E. aurantiacum* than *E. coli* without requiring the use of the expensive material like a specific binding agent, such as an antibody.

It is to be understood that the light-assisted portable sensor for the detection of harmful pathogens is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A portable sensor device comprising:
a sensor chip;
a conducting surface disposed on the sensor chip;
tri-sodium citrate and chitosan-coated gold nanoparticles mounted on the conducting surface; and
a visible light source;
wherein the tri-sodium citrate and chitosan-coated gold nanoparticles have a size between about 10 nm and about 25 nm;
wherein the tri-sodium citrate and chitosan-coated gold nanoparticles cover less than about 35% of the conducting surface; and
wherein the tri-sodium citrate and chitosan-coated gold nanoparticles are spaced about 4 nm to about 15 nm apart.

2. A method of detecting bacteria in an environment using the portable sensor device of claim 1, the method comprising:
exposing the portable sensor device to the environment;
shining the visible light source on the portable sensor device;
activating the gold nanoparticles with the visible light source; and
detecting bacteria using an electrochemical method.

3. The method of claim 2, wherein the visible light source is physically and electronically coupled with the portable sensor device.

4. The method of claim 2, wherein the electrochemical method comprises observing a current change when the bacteria contact the conducting surface.

5. The method of claim 2, wherein the environment comprises a food product.

6. The method of claim 5, wherein the food product is selected from the group consisting of a fruit, vegetable, processed food, raw meat, surface water, and an animal.

7. The method of claim 2, wherein the bacteria is selected from the group consisting of *E. coli* and *E. aurantiacum*.

8. The method of claim 7, wherein the bacteria is *E. coli*.

9. The method of claim 7, wherein the bacteria is *E. aurantiacum*.

10. A method of making the portable sensor device of claim 1, the method comprising:
cleaning the conducting surface;
synthesizing the tri-sodium citrate and chitosan coated gold nanoparticles;
depositing the tri-sodium citrate and chitosan coated gold nanoparticles on the conducting surface; and
mounting the conducting surface on the sensor chip, and
wherein depositing the tri-sodium citrate and chitosan-coated gold nanoparticles on the conducting surface comprises:
drop-casting three successive layers of a solution containing 26.4 µL of the tri-sodium citrate and chitosan-coated gold nanoparticles on the conducting surface; and
drying the conducting surface at about 80° C. for at least about 14 hours;
wherein the conducting surface has an area of 1 cm$^2$.

11. The method of claim 10, comprising cleaning the conductive surface with a cleaner selected from the group consisting of soap, water, deionized water, ethanol, acetone, and a combination thereof.

12. The method of claim 10, comprising using a wet chemical method to synthesize the tri-sodium citrate and chitosan-coated gold nanoparticles.

13. The method of claim 10, wherein synthesizing the tri-sodium citrate and chitosan-coated gold nanoparticles comprises:
adding a chitosan solution to gold (III) chloride trihydrate to create a first mixture;
adding deionized water to the first mixture to create a second mixture;
heating the second mixture to a boil and maintaining the boil for a period of time;
adding tri-sodium citrate to the boiling mixture;
forming a colloidal solution; and
quenching the colloidal solution to stop a reaction in the colloidal solution.

* * * * *